US00PP25929P3

(12) United States Plant Patent
Korlipara

(10) Patent No.: US PP25,929 P3
(45) Date of Patent: Sep. 22, 2015

(54) *LEUCANTHEMUM* PLANT NAMED 'SNOWBOUND'

(50) Latin Name: *Leucanthemum×superbum*
Varietal Denomination: Snowbound

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 189 days.

(21) Appl. No.: 13/998,165

(22) Filed: Oct. 8, 2013

(65) Prior Publication Data

US 2015/0101091 P1 Apr. 9, 2015

(51) Int. Cl.
*A01H 5/02* (2006.01)
*A01H 5/00* (2006.01)

(52) U.S. Cl.
USPC ..... Plt./285
CPC ..... *A01H 5/00* (2013.01)

(58) Field of Classification Search
USPC ..... Plt./285
See application file for complete search history.

*Primary Examiner* — June Hwu
(74) *Attorney, Agent, or Firm* — Klarquist Sparkman, LLP

(57) ABSTRACT

A new and distinct *Leucanthemum* plant named 'Snowbound' characterized by bright white daisy-type inflorescences, numerous inflorescences with good bloom size, excellent crown count, a low, mounding habit, and excellent vigor.

1 Drawing Sheet

Botanical denomination: *Leucanthemum×superbum.*
Variety designation: 'Snowbound'.

BACKGROUND OF THE INVENTION

The present invention relates to a new and distinct cultivar of *Leucanthemum* and given the cultivar name 'Snowbound'. *Leucanthemum* is in the family Asteraceae. This new cultivar originated from a controlled cross between unknown, unnamed, proprietary *Leucanthemum×superbum* seedlings. This was part of a controlled breeding program to get dwarf *Leucanthemum. Leucanthemum* 'Snowbound' was selected for its bright white daisy inflorescences and its clean, low habit.

Compared to *Leucanthemum×superbum* 'Daisy Duke', U.S. Plant Pat. No. 21,914, the new cultivar is much shorter.

Compared to *Leucanthemum×superbum* Darling Daisy™ (unpatented) the new variety has a more rounded habit, larger number of flowering stems, larger inflorescences, and greater vigor.

This new *Leucanthemum* cultivar is distinguished as unique with its:

1. bright white daisy-type inflorescences,
2. numerous inflorescences with good bloom size,
3. excellent crown count,
4. a low, mounding habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 2 year old plant growing in full sun in the trial field in early July in Canby, Oreg.

DETAILED PLANT DESCRIPTION

The following is a detailed description of the new *Leucanthemum* cultivar based on observations of 2-year-old specimens growing in the trial in full sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition.

Plant:

*Type.*—Herbaceous perennial.
*Hardiness.*—USDA Zones 5 to 9.
*Size.*—53 cm wide and 43 cm tall to top of inflorescences.
*Form.*—Basal clump.
*Number of crowns.*—40.
*Vigor.*—Excellent.

Stem (flowering):

*Type.*—Ascending, 1 to 4 branches per stem.
*Size.*—Grows to about 40 cm tall to a terminal inflorescence and 5 mm wide at base.
*Internode length.*—About 1 cm.
*Surface texture.*—Pubescent.
*Strength.*—Excellent.
*Color.*—Yellow Green 147B.

Leaf:

*Type*.—Simple.

*Shape*.—Lanceolate.

*Arrangement*.—Alternate.

*Blade size*.—Grows to 8.5 cm long and 18 mm wide.

*Margins*.—Serrate.

*Apex*.—Acute.

*Base*.—Clasping.

*Petiole*.—Sessile.

*Surface texture*.—Pubescent on both sides.

*Venation*.—Pinnate, main vein top side Yellow Green 147B, bottom side Yellow Green 147C.

*Color*.—Topside Yellow Green 147A, bottom side Yellow Green 147B.

Inflorescence:

*Type*.—Composite on terminal stalked heads.

*Number of inflorescences per plant*.—About 80.

*Size*.—Grows to 8 cm wide and 1.7 cm deep.

*Form*.—Ray florets are held horizontally, mature disc is rounded.

*Immature inflorescence*.—2 cm wide and 2 cm deep, ray florets held vertically and cupped inwards, White NN155A.

*Ray florets*.—With 1 pistil and no stamen, about 22 in number, oblong to oblanceolate, tip with 3 small lobes, margins entire, base attenuate, grows to 40 mm long and 9 mm wide, glabrous and White NN155D on both sides; pistil 5 mm long, ovary 2 mm long, Yellow Green 147D, style 3 mm long, Yellow Green 149D, 2 branched stigma 0.5 mm long, Yellow 13B.

*Disc*.—Slightly concave becoming convex, becoming 10 mm deep and 30 mm wide with maturity, Yellow Orange 14B.

*Disc florets*.—About 440 in number, each 7 mm long and 1.5 mm wide; corolla tubular, 4.5 mm long and 1.5 mm wide, 5 lobed, inside and out glabrous and Yellow Orange 13B on top 1 mm and Yellow Green 145C on middle 2 mm and Yellow Green 147B on bottom; pistil 1, 5.5 mm long, ovary 2.5 mm long and Yellow Green 145D, style 2 mm long, Yellow Green 145C, 2 branched stigma 1 mm long, Yellow Orange 13B; stamen 5 in number, 4 mm long, filaments 2 mm long, Yellow Green 150D, anthers 2 mm, Yellow Orange 17A, pollen Yellow Orange 13A.

*Involucral bracts*.—In 3 imbricate whorls, area 2.5 cm wide and 5 mm deep, lobes ovate to lanceolate in shape, grow to 6 mm long and 3 mm wide, Green 147B with margin membranous and Brown 200B, tip acute, glabrous on both sides.

*Receptacle*.—Grows to 12 mm wide and 3 mm deep, Yellow Green 145D.

*Bloom period*.—July through August in Canby, Oreg.

*Fragrance*.—Very slight.

*Lastingness*.—Each inflorescence lasts about two weeks in Canby, Oreg.

Seeds: Average number of 15 seeds/head, each 3 mm long and 2 mm wide, oval, Brown 200C.

*Fertility*.—Good.

Disease and pests: No problems have been found in Canby, Oreg. in the last 4 years. No known resistances to pests or diseases.

I claim:

1. A new and distinct *Leucanthemum* plant as herein illustrated and described.

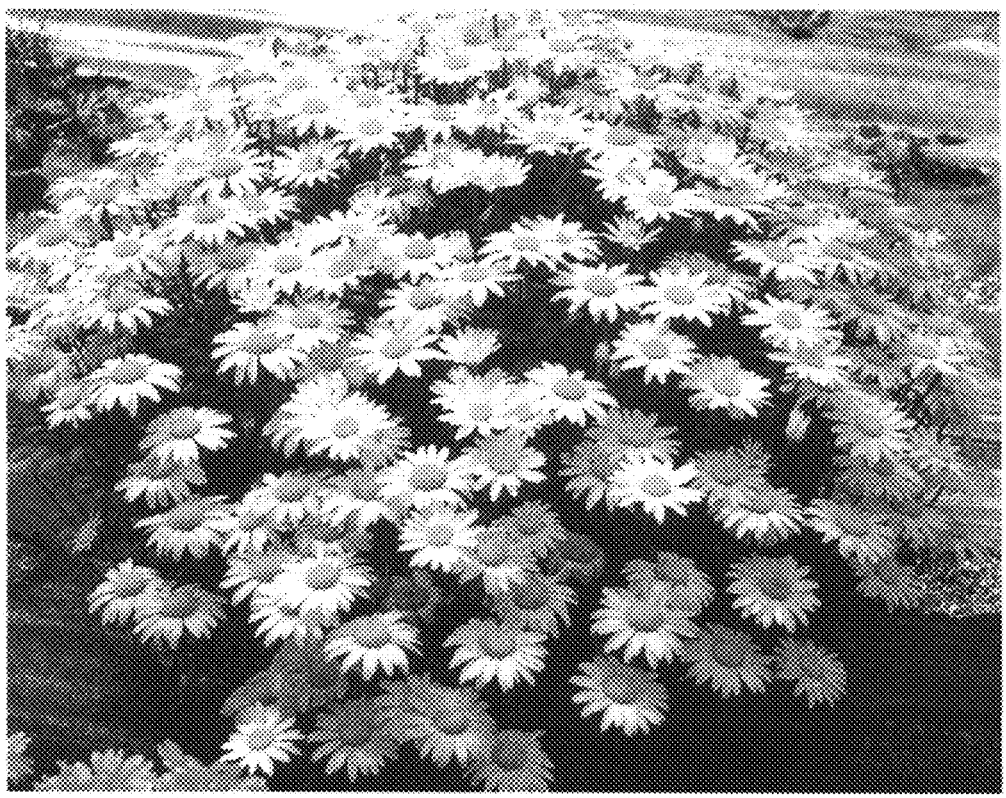

* * * * *